US009033703B2

(12) United States Patent
Rohner et al.

(10) Patent No.: US 9,033,703 B2
(45) Date of Patent: May 19, 2015

(54) DENTAL FURNACE

(75) Inventors: Gottfried Rohner, Altstätten (CH);
Walter Pokorny, Gais (AT); Robert Grünenfelder, Eschen (LI); Frank Rothbrust, Frastanz (AT)

(73) Assignee: Ivoclar Vivadent AG, Schaan (LI)

( * ) Notice: Subject to any disclaimer, the term of this patent is extended or adjusted under 35 U.S.C. 154(b) by 1161 days.

(21) Appl. No.: 12/380,905

(22) Filed: Mar. 5, 2009

(65) Prior Publication Data
US 2009/0226855 A1    Sep. 10, 2009

(30) Foreign Application Priority Data

Mar. 5, 2008    (DE) .......................... 10 2008 012 578

(51) Int. Cl.
| *F27D 9/00* | (2006.01) |
| *A61C 13/20* | (2006.01) |
| *C04B 35/111* | (2006.01) |
| *C04B 35/486* | (2006.01) |
| *C04B 35/64* | (2006.01) |
| *F27B 17/02* | (2006.01) |

(52) U.S. Cl.
CPC ............... *A61C 13/20* (2013.01); *C04B 35/111* (2013.01); *C04B 35/486* (2013.01); *C04B 35/64* (2013.01); *C04B 2235/656* (2013.01); *C04B 2235/6562* (2013.01); *F27B 17/025* (2013.01)

(58) Field of Classification Search
USPC ..................................... 432/4, 120
See application file for complete search history.

(56) References Cited

U.S. PATENT DOCUMENTS

| 4,370,878 A | 2/1983 | Carrieri |
| 4,970,050 A | 11/1990 | Groll et al. |
| 5,072,360 A | 12/1991 | Knorpp et al. |

(Continued)

FOREIGN PATENT DOCUMENTS

| DE | 82 02 852.4 U1 | 6/1982 |
| DE | 8208852 U | 10/1982 |

(Continued)

OTHER PUBLICATIONS

"Alumina-silica paper" http://www.zrci.com/aspa.htm.*

(Continued)

*Primary Examiner* — Alissa Tompkins
*Assistant Examiner* — Nathaniel Herzfeld
(74) *Attorney, Agent, or Firm* — Ann M. Knab; Thad McMurray

(57) ABSTRACT

The invention relates to a dental furnace wherein a firing chamber is heated up in a first heating-up period at a first heating-up rate of more than 50° K/min, in particular more than 100° K/min, which heats the furnace to at least 1000° C., in particular to 1100-1250° C. The first heating-up period is followed by an intermediate heating period, which is at least five minutes long, in particular at least ten minutes long, the gradient or heating-up rate of which is adapted to the material to be sintered in the dental furnace (10), and wherein this is followed by an end heating-up period (44) during which heating up is effected at a heating-up rate of more than 30° K/min, in particular approximately 50° K/min, and wherein during this the furnace temperature is held for at least five minutes, in particular for at least 25 minutes, above the temperature toward the end of the first heating-up period, and wherein forced cooling of the furnace (10) is performed after this.

7 Claims, 2 Drawing Sheets

(56) References Cited

U.S. PATENT DOCUMENTS

| | | | |
|---|---|---|---|
| 5,775,912 | A | 7/1998 | Panzera et al. |
| 5,788,485 | A | 8/1998 | Grunenfelder |
| 5,905,937 | A * | 5/1999 | Plucknett et al. ............... 419/12 |
| 6,025,065 | A * | 2/2000 | Claussen et al. ........... 428/307.7 |
| 6,126,895 | A * | 10/2000 | Dennis et al. ..................... 419/9 |
| 2002/0106611 | A1 | 8/2002 | Bhaduri et al. |
| 2005/0201795 | A1 * | 9/2005 | Kawachi et al. .............. 399/406 |
| 2005/0261795 | A1 * | 11/2005 | Ghosh et al. .................. 700/118 |
| 2006/0191916 | A1 * | 8/2006 | Stephan et al. ............... 219/686 |
| 2007/0023971 | A1 * | 2/2007 | Saha et al. .................... 264/432 |
| 2008/0213611 | A1 * | 9/2008 | Asgari .......................... 428/566 |

FOREIGN PATENT DOCUMENTS

| | | |
|---|---|---|
| DE | 38 41 902 C1 | 11/1989 |
| DE | 3841902 C1 | 11/1989 |
| DE | 3831539 A1 | 3/1990 |
| DE | 3831539 C3 | 3/1990 |
| DE | 19753837 A1 | 6/1999 |
| DE | 699 02 570 T2 | 4/2003 |
| DE | 69902570 T2 | 4/2003 |
| EP | 0 337 897 A1 | 10/1989 |
| EP | 0337897 A1 | 10/1989 |
| EP | 0985893 B1 | 8/2002 |
| JP | 2-116366 A | 1/1990 |
| JP | 06-121800 A | 5/1994 |
| JP | 06-269466 A | 9/1994 |
| JP | 7-32787 B | 4/1995 |
| JP | 10-033564 A | 2/1998 |
| JP | 10-075964 A | 3/1998 |
| JP | 2000-329477 A | 11/2000 |

OTHER PUBLICATIONS http://web.archive.org/web/20010213232049/http://www.zrci.com/aspa.htm.*

Menezes et al: "Microwave hybrit fast sintering of porcelain bodies" Journal of Material Procedding Technology, Elsevier, NL Bd.190, Nr. 1-3, May 11, 2007pp. 223-229.

Menezes, R.R., et al., Microwave hybrid fast sintering of porcelain bodies, Journal of Materials Processing Technology, 2007, vol. 190, pp. 223-229.

Agarwal, G., et al., Microstructural development of ZnO using rate-controlled sintering dilatometer, Journal of Materials Research, Mar. 1996, vol. 11, No. 3, pp. 671-679.

Programat P300, Operating Instructions, Ivoclar Vivadent AG, version 2, Mar. 2006, pp. 1-34.

Dekema, Dental Furnace Austromat 3001 Manual, Version Jan. 2005, pp. 4-5 and 10-15.

Dekema, Dental Furnace Austromat D4 Manual, Version Aug. 2005, pp. 4-5, 21-23, and 28-33.

Dekema, Dental Furnace Austromat 3001 press-i-dent Manual, Version Jan. 2005, pp. 4-5 and 10-16.

Dekema, Technical drawing of the combustion chamber insulation of Austromat 3001, 1 page.

Dekema, Order confirmation for Rath company of Austromat 3001 and Safety Data Sheet, 11 pages.

Dekema, Notice of Opposition filed in DE 10 2008 012 578.4, 13 pages.

* cited by examiner

DENTAL FURNACE

CROSS-REFERENCE TO RELATED APPLICATIONS

This application claims foreign priority benefits under 35 U.S.C. §119(a)-(d) from German patent application ser. no. P 10 2008 012 578.4 filed Mar. 5, 2008.

TECHNICAL FIELD

The invention relates to a dental furnace which is heated up in stages and also cooled down to a method for heating up and cooling down, and more particularly to such a furnace used for sintering dental materials.

BACKGROUND OF THE INVENTION

A dental furnace of this type and a method of this type have long been known. Precisely for sintering adapted dental materials it is important to cause the heating up, the actual firing, and indeed the cooling down as well, to proceed according to a predetermined and reproducible scheme in order on the one hand to ensure the required material compaction, but on the other hand also to ensure that the shrinkage takes place uniformly to the entire extent.

For this purpose, the temperature in the interior of the dental furnace is typically controlled with a precisely determined temperature profile. For this purpose, the heating elements are connected to a corresponding control device, and a temperature sensor is normally used.

The temperature sensor is typically arranged in the upper region of the firing chamber serving as working space, the restorations being placed there.

Temperature sensors can therefore be arranged in or on the wall of the firing space, and it is known to use special calibration devices to ensure that the temperature in the interior of the dental furnace follows a predetermined temperature profile.

On the other hand, the heat capacity of the introduced mass is a parameter that influences the heating-up profile of the dental material. The heating-up rate is typically lower if large masses are used, and higher if small masses are used. In order to compensate for this effect, it is possible to detect the introduced mass beforehand and to provide calibration curves for different masses. However, this is complicated and greatly dependent on the operator's care.

Moreover, the mass of the introduced dental material cannot usually be ascertained exactly.

Therefore, it is known to work with a comparatively low heating-up rate in order to provide for the dental materials the possibility of bringing about a homogeneous temperature compensation, irrespective of what mass is present. Although this method is good in principle, it is diametrically opposite to the desires in the dental laboratory to save costs by means of a short production cycle.

Furthermore, U.S. Pat. No. 6,025,065 has, however, also disclosed combining an extremely high heating-up rate of more than 100 1C/min with a high temperature of 1300° C. to 1600° C. Although the sintering furnace therein is in principle extremely well suited to the rapid sintering of materials, the dimensional accuracy thereof is of lesser relevance. Such a furnace is not suitable, however, for dental materials.

OBJECTS AND SUMMARY OF THE INVENTION

Against this background, the invention is based on the object of providing a dental furnace which are particularly well suited to the production of dental materials.

The invention provides for heating up a dental furnace with a firing chamber at an extremely high first heating-up rate until a temperature corresponding to a presintering temperature has been reached. What can be achieved by means of the presintering expedient according to the invention is that the sintering material can be processed after the presintering.

Surprisingly, by means of the rapid heating up according to the invention at the first high heating-up rate, which is ended only at a temperature of 1000° C., 1100° C. or even 1200° C., the sintering cycle can be significantly accelerated without disadvantages occurring in the case of the final strength, on the one hand, or in the case of the accuracy of fit, on the other hand.

Surprisingly, the observation even becomes apparent that the final strength is increased by this rapid heating up in comparison with a slower heating up.

According to the invention, the first heating up with the high first heating-up period is followed by an intermediate heating period, the heating-up rate or temperature gradient of which is significantly smaller than that of the initial heating-up period. By way of example, the temperature gradient during the intermediate heating period can be 2° K, 3° K, 5° K or 10° K/min.

After the intermediate heating period, the duration of which can be adapted to the requirements in wide ranges and can be for example 5 min, 10 min, 20 min or 30 min, an end heating-up period is provided, the temperature gradient or heating-up rate of which is likewise significantly higher and can be for example at least 20° K/min, but preferably approximately 50° K/min.

The temperature difference between the temperature toward the end of the intermediate heating period and the end temperature toward the end of the end heating-up period is comparatively small and is for example somewhat more than 100° C., or 200° C. for example, without any deterioration in the accuracy of fit.

By contrast, the accuracy of fit is significantly improved by the low heating-up rate during the intermediate heating period.

According to the invention it is particularly expedient for the end of the heating-up period to be followed by a holding period, during which the temperature in the firing chamber is held substantially at the end temperature toward the end of the heating-up period or just below that. The final density and the strength of the dental material can be significantly improved by this measure.

The realization of a particular dental furnace is particularly expedient for the configuration of the temperature profile according to the invention. In order to be able to realize the high temperature gradient desired, a dental furnace according to the invention preferably has a low heat capacity between the heating elements and the firing space, which heat capacity may be composed for example of a rather thin insulation material, for example quartz glass. The comparatively effective heating elements would permit the dental furnace to be heated up to 1600° C. from room temperature within somewhat more than 10 min, where it is understood that a particular temperature profile is sought according to the invention.

The dental furnace according to the invention takes account particularly of the fact that the sintering in the case of the dry sintering takes place in three stages, namely an initial stage, an intermediate stage and an end stage, wherein the sintering rate, that is to say the contraction of the material per unit time, is the highest in the intermediate stage, such that for example 90% of the final density can be achieved at the end of the intermediate stage.

According to the invention it is preferred to allow the initial stage to be undergone as early as during the presintering, such that the sintering rate during sintering to completion only undergoes the intermediate and end stages.

In this connection it is expedient according to the invention if a low heat capacity is also used for the thermal insulation, wherein it is also possible, for example, to keep the thermal insulation layer at a distance from the heating element, such that the capacity no longer plays a part. This additionally has the particular advantage that the cooling down of the heating elements can be significantly improved by convection. By way of example, it is also possible to realize rear-ventilated heating elements, that is to say heating elements in which the air flow with the furnace hood open also contributes to the cooling of the heating elements from the side remote from the firing chamber.

The dental furnace according to the invention can be a furnace with a firing chamber which can be removed from a substructure. In this case, either a lifting mount or a pivoting mount or a combination of these mounts is possible. One example of such a mount can be seen from U.S. Pat. No. 5,788,485.

In addition to the convection cooling it is also possible to use active cooling by means of a fan in order in this respect in any case to achieve the desired cooling-down rate. This holds true particularly when a dental furnace in a traditional form with a firing chamber door is used, a dental firing furnace with a flat bearing surface and a removable firing hood being preferred.

According to the invention, the temperature and duration of the precompaction, by means of the presintering, can be adapted to the requirements within wide ranges. The presintering is preferably effected in a separate process step beforehand on the dental block. By way of example, the presintering can be effected at the final temperature of the first heating-up period, that is to say for example at 1100° C. or at 1250° C. This presintering has the advantage that the presintered material can still be mechanically processed since the hardness is significantly lower than in the material sintered to completion.

By comparison with high-temperature sintering furnaces known per se, it is particularly preferred according to the invention that the cycle time is significantly reduced, by comparison with the typical 8 to 10 hours for sintering to completion and cooling down in the case of known high-temperature sintering furnaces.

According to the invention, it is possible, by contrast, to reduce the total cycle time to less than three hours, including the cooling down, and in a modified embodiment of the solution according to the invention, the total cycle time can be reduced to less than 90 min despite the use of high-strength dental ceramic with firing temperatures of more than 1500° C.

An alternative embodiment provides for using, instead of a sintering furnace, a microwave furnace for the realization of the dental furnace according to the invention.

The firing curve accelerated according to the invention is distinguished in diagrammatic representation by a "block form with shoulders". The first heating-up period is extremely short with a large temperature gradient, as is the end cooling-down phase with a likewise steep temperature gradient. A temperature phase above 1100° C. that is significantly lengthened in comparison with the total length of the heating curve is thus available, which can then be optimized according to the invention. Thus, it is expedient according to the invention if the "high-temperature phase" takes up 68%, that is to say in this respect just below 70%, of the total firing cycle in the case of a short firing curve of less than three hours, and even above 80% in the case of a standard firing curve, in each case relative to the heating up from room temperature and the cooling down to room temperature and the duration for which the firing temperature of more than 1100° C. is complied with.

By obviating kiln furniture, it is possible to further reduce the heat capacity or thermal mass in relation to kilns having kiln furniture. It is also particularly expedient according to the invention if, instead of passive cooling, active cooling is also effected precisely in the interspace between the thermal insulation and the heating element, and also within the open firing space, such that the desired cooling-down rate can be achieved.

It is preferred in this connection if in this respect rear-ventilated firing chamber is embodied expediently in terms of flow, such that the active ventilation can be realized with a comparatively low fan rotational speed and thus very quietly.

For this purpose, two flow ducts are preferably provided, namely a rear-ventilation flow duct and a flow duct through the firing chamber, wherein it is understood that the convection cooling can also be produced at least in part—precisely at high temperatures.

In a further preferred configuration it is provided that the sintering material to be sintered is heated up in a first heating-up period at a heating-up rate of more than 50° K/min, wherein, between the end of the first heating-up period and the beginning of an end heating period there is an intermediate heating period at a heating-up rate significantly lower than 50° K/min, in particular less than 10° K/min, and wherein the first heating-up period and the end heating period are set in a material-independent manner, and wherein the intermediate heating period is defined, with regard to its length and its heating-up rate, in a manner dependent on the material to be sintered.

In a further preferred configuration it is provided that the maximum temperature in the heating chamber is approximately 1600° C. and the furnace can be heated up to 1600° C. proceeding from room temperature in its heating chamber, within less than 30 minutes.

In a further preferred configuration it is provided that the intermediate heating-up rate is lower than the initial heating-up rate by approximately a power of 10, in particular by a factor of 10 to 50.

In a further preferred configuration it is provided that a heating chamber of the furnace is surrounded by a heat-resistant insulation, in particular a pressed shaped part composed of fiber, the wall thickness of which is preferably between 15 and 25 mm.

In a further preferred configuration it is provided that the intermediate heating period is chosen in terms of the temperature and/or the time such that it covers the intermediate stage of the sintering process of the dental material to be sintered, in which the sintering rate, plotted against the temperature/time, is the highest.

In a further preferred configuration it is provided that the dental material to be fired is presintered and/or precompacted and prior to the actual sintering has a strength which is significantly lower than, in particular less than half the magnitude of, the final strength of the sintering material.

In a further preferred configuration it is provided that the initial heating-up rate is chosen such that it corresponds to the maximum heating-up rate at which no overshoot arises upon the transition from the initial heating-up period to the intermediate period, but is at least 50° K min$^{-1}$.

In a further preferred configuration it is provided that, after a holding time has elapsed, the furnace cools down at a first cooling-down rate, which is less than the heating-up rate of the initial heating-up period and greater than the heating-up rate of the intermediate heating-up period, and wherein a higher, second cooling-down rate is set after this.

In a further preferred configuration it is provided that the dental furnace is a microwave furnace.

In a further preferred configuration it is provided that a method wherein a heating chamber is heated up in a first heating-up period at a first heating-up rate of more than 50° K/min, in particular approximately 100° K/min, which heats up the furnace to at least 1000° C., in particular to 1100° C. to 1250° C., wherein the first heating-up period is followed by an intermediate heating period, which is at least five minutes long, in particular at least ten minutes long where the gradient or heating-up rate thereof is subsequently adapted to the material to be sintered in the furnace, and wherein this is followed by an end heating-up period, during which heating up is effected at a heating-up rate of more than 20° K/min, in particular approximately 50° K/min, and wherein during this the furnace temperature is held for at least five minutes, in particular for 25 minutes, above the temperature toward the end of the first heating-up period, and wherein forced cooling of the furnace is performed after this.

In a further preferred configuration it is provided that a method wherein the sintering material to be sintered is heated up in a first heating-up period at a heating-up rate of more than 50° K/min, wherein, between the end of the first heating-up period and the beginning of an end heating period, preheating is effected for an intermediate heating period at a heating-up rate significantly lower than 50° K/min, in particular less than 10° K/min, and wherein the first heating-up period and the end heating period have been or are set in an object-independent manner, and wherein the intermediate heating period is defined, with regard to its length and its heating-up rate, in a manner dependent on the material to be sintered.

In a further preferred configuration it is provided that dental tooth replacement material is sintered in dry fashion or in liquid sintering, wherein the sintering material comprises an oxide ceramic which is composed, in particular, of $ZrO_2$, of $Al_2O_3$ and compositions thereof and comprises, in particular, a doping auxiliary.

In a further preferred configuration it is provided that, starting when the holding time has elapsed, forced cooling of the furnace is performed, which leads to the cooling down of the tooth replacement material to a removal temperature, in particular of approximately 400° C., in less than 60 minutes, in particular 20 to 60 minutes.

Further advantages, details and features will become apparent from the description below of an exemplary embodiment with reference to the drawing, in which:

DETAILED DESCRIPTION

Figure 1:
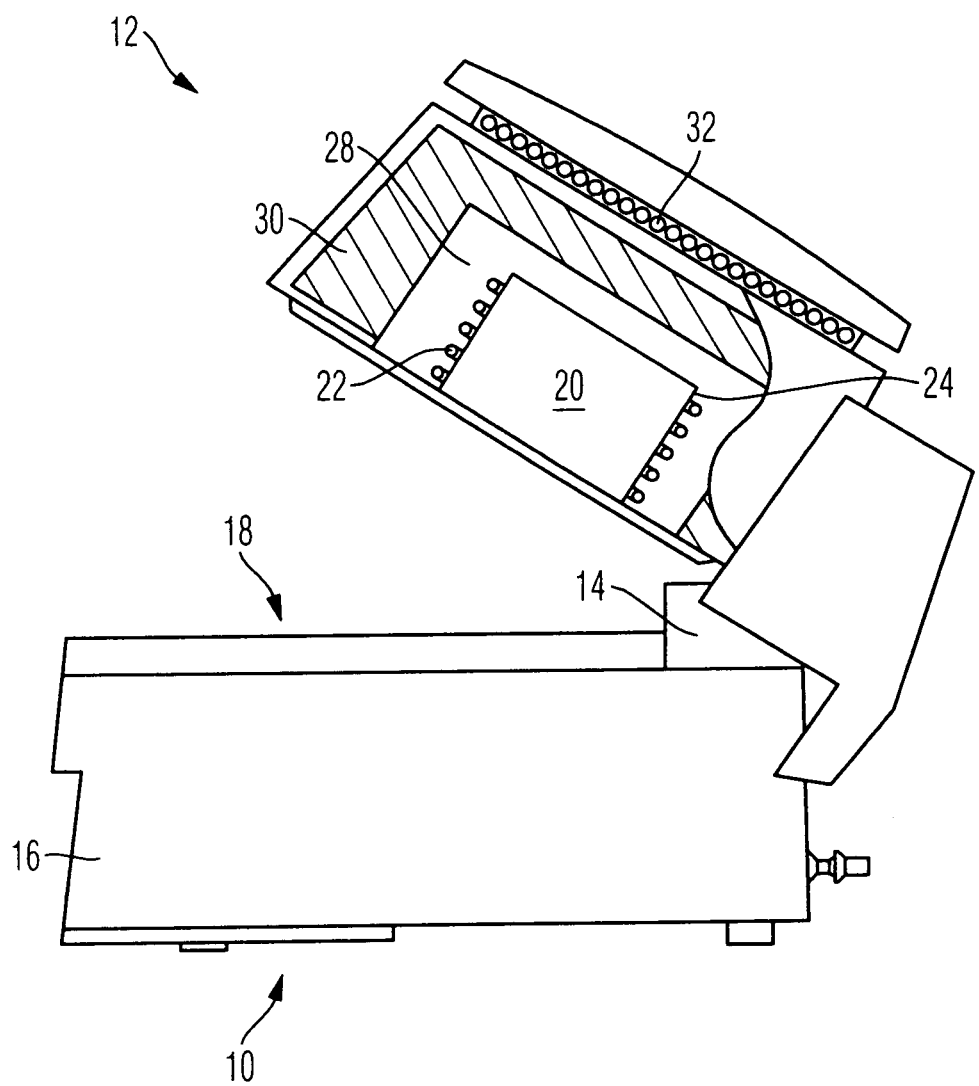
FIG. 1 shows a schematic and partially cut-away view of a dental furnace according to the invention.

The dental furnace 10 illustrated in FIG. 1 has a furnace hood 12, which is mounted on a furnace lower part 16 by means of a pivoting articulated joint 14. The lower part 16 has on its top side a bearing surface 18, which is intended for receiving the dental material to be fired. A firing chamber 20 is provided in the furnace hood 12, and it extends in the manner of a rather flat cylinder and, with the furnace hood 12 closed, is closed off at the bottom by the bearing surface 18, such that the bearing surface 18 forms the bottom of the firing chamber 20.

The firing chamber 20 is surrounded annularly or spirally by heating elements 22.

According to the invention, particularly powerful heating elements are provided, which are designed such that they are fundamentally able to heat up the furnace from room temperature to 1600° C. within approximately a quarter of an hour. The dental furnace accordingly has a max. temperature gradient of 120° K/min.

The heat capacity of the firing chamber 20 and of the parts surrounding the firing chamber 20 is low.

The heating elements 22 are additionally significantly rear-ventilated. An air space 28 is provided for this purpose, said air space surrounding the heating elements 22 and thus the firing space 20 on all sides. The air space 28 is extremely large and takes up a considerable part of the interior of the furnace hood 12. The furnace hood 12 has a thermal insulation layer 30 surrounding the air space 28, which layer—even though this cannot be seen in FIG. 1—can also have perforations forming air ducts in order to facilitate the air flow via air outlets 32 in the upper region of the furnace hood 12.

The dimensioning both of the air space 12 and of the thermal insulation layer 30, can be adapted to the requirements within wide ranges, it also being possible to work with an extremely thin thermal insulation layer of just 15 mm, for example.

The dental material preferably provided is applied to the bearing surface 18 according to the invention. After the furnace hood 12 has been closed, the heating element 22 is switched on with max. power, such that the firing chamber 20 is heated extremely rapidly to 1200° C., for example. This temperature may substantially correspond to the presintering temperature. After this, during an intermediate heating period, the temperature is increased with a small temperature gradient until a temperature of approximately 100° C. below the final temperature has been reached. After this, the temperature is increased extremely rapidly again to the final temperature and after this is held for a predetermined time duration, wherein the holding time may depend both on the applied amount of dental material and on further parameters.

After this, the temperature is reduced, to be precise preferably firstly without active cooling, wherein the active cooling is switched on when the presintering temperature has been reached again, such that the cooling proceeds more rapidly starting from said temperature until room temperature is reached.

As an alternative, in an even more highly accelerated firing cycle, the cooling down can take place directly after the holding time with active cooling, such that the cooling-down period overall is shortened further.

An initial heating-up period 40, which is ended at approximately 1100° C. in accordance with curve 2, is followed by an intermediate heating period 42, which performs heating up to approximately 1350° C.

After this, an end heating-up period 44 is provided, which increases the temperature to 1500° C., which final temperature is reached 100 min after the beginning of the firing cycle in the case of "curve 2".

During the holding time 46 of approximately 30 min, the temperature is held at 1500° C. and, during the initial cooling-down period 48, the temperature is lowered to 1100° C. within less than 30 min.

After this, the end cooling period 50 is provided, by means of which the temperature is lowered to room temperature within likewise somewhat less than half an hour.

Figure 2:
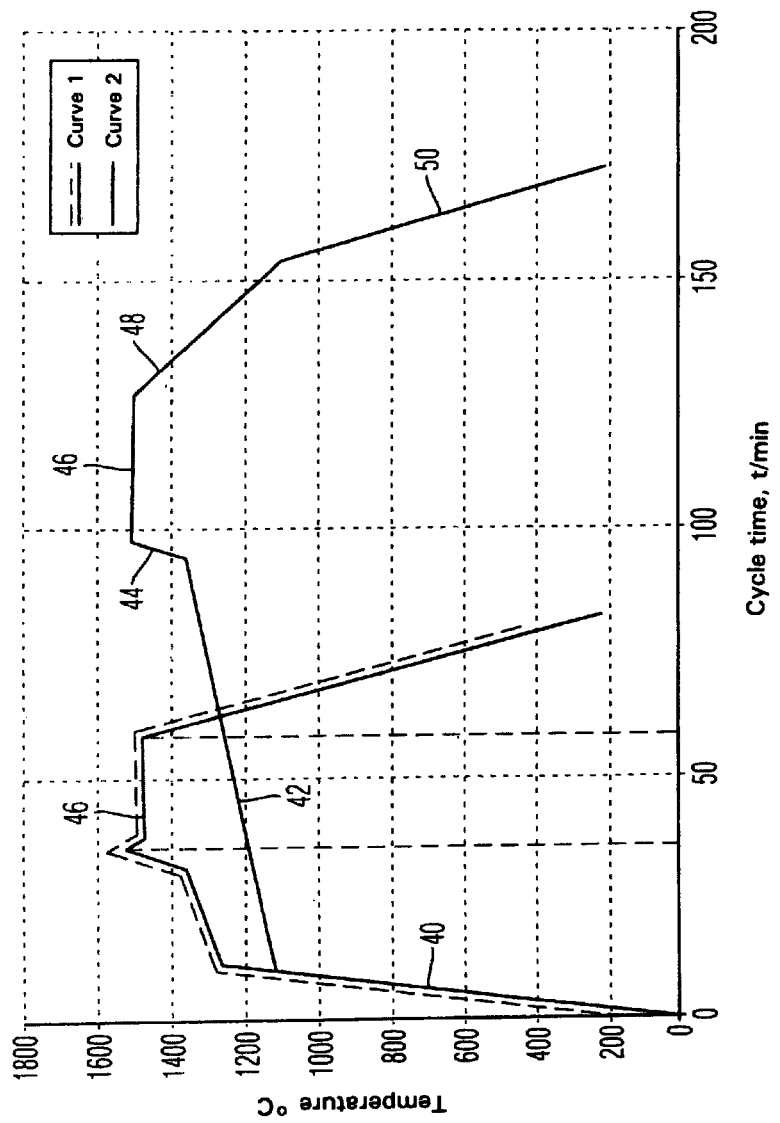
FIG. 2 shows two exemplary embodiments of firing curves for the dental furnace according to the invention.

This firing cycle according to the invention is illustrated in two embodiments in FIG. 2. Accordingly, the following firing curve results for the curve designated as "curve 2":

| Ramp | Temperature/ C. | Rate/ K min⁻¹ | Time/ min | Total/ min |
|---|---|---|---|---|
| 0 | 25 | | | |
| 1 | 1100 | 100 | 10.75 | 10.75 |
| 2 | 1350 | 3 | 83.33 | 94.08 |
| 3 | 1500 | 50 | 3.00 | 97.08 |
| 4 | 1500 | 0 | 30.00 | 127.08 |
| 5 | 1100 | −15 | 26.67 | 153.75 |
| 6 | 200 | −50 | 18.00 | 171.75 |

Firing Curve 2

| Ramp | Temperature/ C. | Rate/ K min⁻¹ | Time/ min | Total/ min |
|---|---|---|---|---|
| 0 | 25 | | | |
| 1 | 1250 | 100 | 12.25 | 12.25 |
| 2 | 1350 | 5 | 20.00 | 32.25 |
| 3 | 1500 | 50 | 3.00 | 35.25 |
| 4 | 1500 | 0 | 25.00 | 60.25 |
| 5 | 1100 | −25 | 16.00 | 76.25 |
| 6 | 200 | −46.6 | 19.31 | 95.56 |

Firing Curve 1

The total firing curve is reduced even further in the modified embodiment in accordance with "curve 1" to approximately 95 min, wherein a substantially trapezoidal curve profile is provided in both cases, each having a high initial heating-up rate and an equally or almost equally high end cooling-down rate. This is also evident from the table above.

In contrast to the firing cycle in accordance with curve 2, an overshoot of the heating power to a temperature of, for example, 50° C. above the temperature of the holding time 46 is provided in the case of curve 1.

Surprisingly, the strength is increased by the rapid heating-up to the presintering temperature, or alternatively to 1250° C., while there is no measurable influence on the accuracy of fit. By contrast, the accuracy of fit and hence the distortion are improved by the slow heating up during the intermediate heating period, while the strength is not adversely affected. By contrast, the end heating up, for example by 150° C., to the end heating up temperature, which may lie between 1500° C. and 1600° C., has no particular influence on the strength and no influence at all on the accuracy of fit.

By contrast, the comparatively long holding time has a very great influence on the strength and in particular also on the final density, and the relatively slow cooling-down to the presintering temperature as provided in accordance with curve 2 also has a measurable influence on the strength, while the subsequent cooling down to room temperature has practically no further influence on the strength or the density.

According to the invention, it is therefore possible to realize a dental furnace with a short firing cycle, yet particularly attractive firing results.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the terms as used in the claims are intended to include not only the designs illustrated in the drawings of this application and the equivalent designs discussed in the text, but are also intended to cover other equivalents now known to those skilled in the art, or those equivalents which may become known to those skilled in the art in the future.

What is claimed is:

1. A total firing method for sintering a dental material comprising:
   heating a heating chamber in a first heating-up period at a first heating-up rate of more than 50° K/min, which heats up the furnace to at least 1000° C.,
   continuing to heat the chamber in an intermediated heating period, wherein the first heating-up period is followed by the intermediate heating period, which is at least five minutes long, and
   continuing to heat the chamber in an end heating-up period, wherein the intermediate heating period is followed by the end heating-up period, during which heating-up is effected at a heating-up rate of more than 20° K/min, wherein the end heating-up period has a rate that is slower than the first heating-up rate, and
   holding the temperature in the end heating period for at least five minutes, above a temperature that has been measured at the end of the first heating-up period, and
   force cooling the furnace after the end heating period,
   wherein the total firing method takes place over a time span from a start of the first heating-up period at room temperature to the cooling down of the heating chamber to room temperature,
   wherein the heating chamber has a temperature higher than 1100° C. at least 68% of the time span of the total firing method,
   wherein during the intermediate heating period about 90 percent of final density of the dental material being sintered is achieved.

2. The method as claimed in claim 1, wherein, starting when the holding time has elapsed, forced cooling of the furnace is performed, which leads to the cooling down of the dental material to a removal temperature of approximately 400° C., in less than 60 minutes.

3. The total firing method as claimed in claim 1, wherein the first heating-up rate is approximately 100° K/min and wherein the furnace is heated up to 1100° C. to 1250° C. in the first heating-up period,
   wherein the intermediate heating period is at least ten minutes long,
   wherein the end heating-up period is effected at a heating-up rate of approximately 50° K/min, and
   wherein during the end heating-up period the furnace temperature is held for 25 minutes above the temperature toward the end of the first heating-up period.

4. The method according to claim 2, wherein the cooling of the furnace (10) is performed in 20 to 60 minutes.

5. A method wherein a dental material to be sintered is heated up in a first heating-up period at a heating-up rate of more than 50° K/min,
   continuing to heat the dental material in an intermediate heating period at a heating-up rate lower than 50° K/min, wherein, between the end of the first heating-up period and the beginning of an end heating period, preheating is effected in the intermediate heating period wherein the first heating-up period and the end heating period are set in an object-independent manner,
   wherein the intermediate heating period is defined, with regard to its length and its heating-up rate, in a manner dependent on the material to be sintered,
   wherein during the intermediate heating period about 90 percent of final density of the dental material being sintered is achieved, and wherein the end heating-up period has a rate that is slower than the heating-up rate in the first heating-up period.

6. The method as claimed in claim 5, wherein the dental material comprises a dental tooth replacement material and is sintered in dry fashion or in liquid sintering, wherein the dental material comprises an oxide ceramic which is composed of $ZrO_2$, of $Al_2O_3$ and compositions thereof and comprises a doping auxiliary.

7. The method according to claim 5, wherein the heating-up rate of the intermediate heating period is less than 10° K/min.

* * * * *